US012357486B2

(12) United States Patent
Görnert et al.

(10) Patent No.: US 12,357,486 B2
(45) Date of Patent: Jul. 15, 2025

(54) HARD FRAME WITH PIVOTABLE BRIDGE

(71) Applicant: Bauerfeind AG, Zeulenroda-Triebes (DE)

(72) Inventors: Florian Görnert, Zeulenroda-Triebes (DE); Sandro Hebenstreit, Zeulenroda-Triebes (DE); Hans B. Bauerfeind, Zeulenroda-Triebes (DE)

(73) Assignee: Bauerfeind AG, Zeulenroda-Triebes (DE)

( * ) Notice: Subject to any disclaimer, the term of this patent is extended or adjusted under 35 U.S.C. 154(b) by 0 days.

(21) Appl. No.: 16/956,473

(22) PCT Filed: Dec. 21, 2018

(86) PCT No.: PCT/EP2018/086667
§ 371 (c)(1),
(2) Date: Jun. 19, 2020

(87) PCT Pub. No.: WO2019/122364
PCT Pub. Date: Jun. 27, 2019

(65) Prior Publication Data
US 2020/0345529 A1 Nov. 5, 2020

(30) Foreign Application Priority Data
Dec. 22, 2017 (DE) .......................... 102017223757.0

(51) Int. Cl.
A61F 5/01 (2006.01)
(52) U.S. Cl.
CPC .... A61F 5/0123 (2013.01); A61F 2005/0165 (2013.01); A61F 2005/0179 (2013.01)
(58) Field of Classification Search
CPC ............ A61F 5/0123; A61F 2005/0165; A61F 2005/0179; A61F 5/0106; A61F 5/00; A61F 5/01
See application file for complete search history.

(56) References Cited

U.S. PATENT DOCUMENTS 5,092,320 A  3/1992 Maurer
5,286,250 A  2/1994 Meyers et al.
(Continued)

FOREIGN PATENT DOCUMENTS

DE  60205192 T2  4/2006
EP  1302184  4/2003
(Continued)

OTHER PUBLICATIONS

International Search Report and Written Opinion for PCT/EP2018/086667 dated Mar. 20, 2019, with English translation of International Search Report, 12 pages.
(Continued)

Primary Examiner — Ophelia A Hawthorne
Assistant Examiner — Michael Milo
(74) Attorney, Agent, or Firm — Sheppard Mullin Richter & Hampton LLP

(57) ABSTRACT

The invention relates to a hard frame (100) for a joint-bridging extremity joint orthosis, containing two mutually opposed longitudinally extending joint splints (110, 120), the proximal joint arms (113, 123) thereof being connected to one another via a transverse proximal bridge arch (310) and forming a proximal extremity holder (300), and the distal joint arms (112, 122) of which being connected to one another via a transverse distal bridge arch (210) and forming a distal extremity holder (200). According to the invention, at least one of the bridge arches (210) is mounted on joint arm ends (114, 124) of the associated joint arms (112, 122) of the joint splints (110, 120) connecting the bridge arch (210), noreover is mounted pivotably about at least one pivot axis (222) at a joint (220).

7 Claims, 5 Drawing Sheets

(56) References Cited

U.S. PATENT DOCUMENTS

Figure 1:
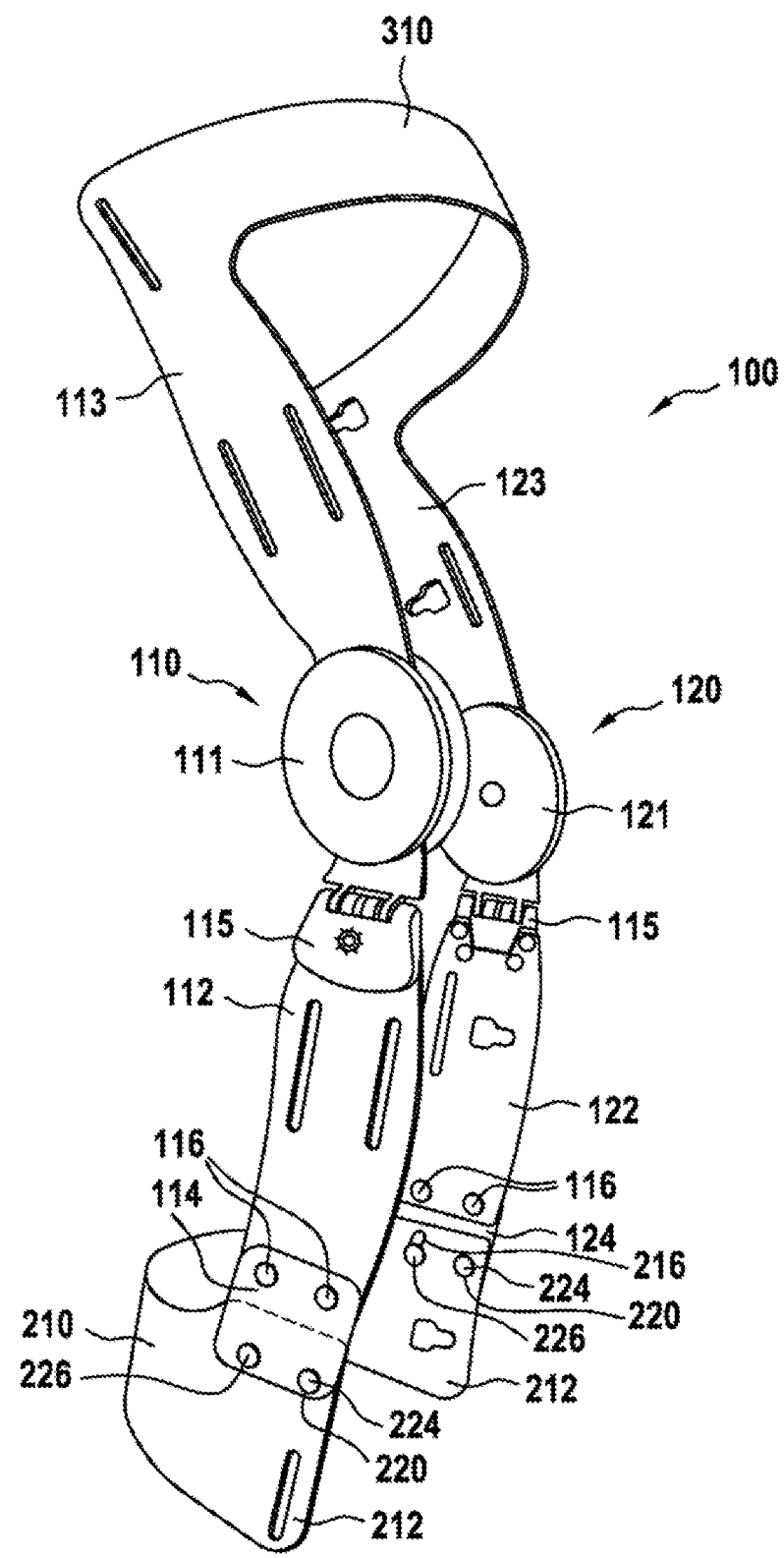

| | | | | |
|---|---|---|---|---|
| 5,743,865 | A * | 4/1998 | Townsend | A61F 5/0123 |
| | | | | 602/26 |
| 8,603,018 | B2 | 12/2013 | Anglada | |
| 9,770,356 | B2 | 9/2017 | Ingimundarson et al. | |
| 9,987,151 | B2 * | 6/2018 | Errico | B25J 9/0006 |
| 10,765,548 | B2 * | 9/2020 | Luo | A61F 5/0123 |
| 2004/0002674 | A1 * | 1/2004 | Sterling | A61F 5/0123 |
| | | | | 602/26 |
| 2008/0208095 | A1 | 8/2008 | Kazmierczak et al. | |
| 2010/0100021 | A1 * | 4/2010 | Einarsson | A61F 5/0106 |
| | | | | 602/23 |
| 2013/0041300 | A1 | 2/2013 | Nace | |
| 2014/0323937 | A1 | 10/2014 | Knecht | |
| 2014/0364782 | A1 * | 12/2014 | Knecht | A61F 5/0125 |
| | | | | 602/16 |
| 2019/0274859 | A1 * | 9/2019 | Boucher | G16H 50/50 |

FOREIGN PATENT DOCUMENTS

| | | | | |
|---|---|---|---|---|
| EP | 3216429 | | 9/2017 | |
| EP | 3216429 A1 * | | 9/2017 | A61F 5/0123 |
| FR | 2862205 A1 * | | 5/2005 | A61F 5/0123 |
| WO | WO 2013/040375 | | 3/2013 | |

OTHER PUBLICATIONS

International Preliminary Report on Patentability for PCT/EP2018/086667 dated Jun. 25, 2020, 7 pages.

* cited by examiner

HARD FRAME WITH PIVOTABLE BRIDGE

CROSS REFERENCE TO RELATED APPLICATIONS

This application is a U.S. National Stage Application under 35 U.S.C. § 371 of International Application No. PCT/EP2018/086667, filed Dec. 21, 2018, which claims priority to DE 102017223757.0, filed Dec. 22, 2017, the contents of which are incorporated to the present disclosure by reference.

The present invention relates to medical joint orthoses for guiding or supporting the joint function on extremity joints, especially knee joint orthoses. The invention provides an improved rigid support frame (hard frame) for forming such a joint orthosis, the hard frame in particular having a frame with a tiltable or pivotable frame bridge.

Joint orthoses according to the invention having a rigid hard frame are known. A joint orthosis hard frame for bridging and thus supporting and guiding an extremity joint, for example the knee joint, is generically formed by two mutually opposed joint splints which bridge the extremity joint to be supported or guided when the orthosis is in the applied state. These joint splints each have a joint that is uniaxially or multiaxially formed in order to largely simulate and follow the anatomical joint movement of the extremity joint. On either side of the joint, the arms of the joint splints are connected to a holder close to (proximal) and distant from (distal) the body, respectively. Each of these holders firmly grips the extremity section close to or distant from the body in order to achieve mechanical coupling with the extremity, arm or leg, hand or foot, in order to convey the desired support function of the joint splints to the bridged joint of the extremity. Extremity holders and joint splints essentially form the unit of this generic hard frame. Such rigid frames are generically connected either directly to the extremity via appropriate straps, in particular in the region of the extremity holders, or alternatively or additionally retrofitted on joint bandages that are tightly fitting on the extremity, that is, mechanically coupled to them.

The problem with such known hard frames is that in the region of the holder of the respective extremity section, that is to say in the case of knee joint orthoses particularly on the lower leg, mechanical overstressing can occur, in particular as a result of pressure or shear stress of the underlying tissue sections. In the favorable case, this leads to an unpleasant feeling of pressure or pain for the wearer of the orthosis, in the unfavorable case to significant tissue injuries, the result of which is that the orthosis can no longer be worn.

On the other hand, it has been shown in many cases that, in order to form a well- supporting orthosis, the two lateral joint splints in the hard frame must be connected to one another by rigid bridges, these frame bridges simultaneously being part of the extremity holder. Such mechanically necessary frame bridges can push into adjacent tissue sections of the extremity when the orthosis is worn. Compensating solutions consist of providing pads on the frame bridges that distribute and reduce the pressure on the underlying tissue. Such solutions are unfavorable because they simultaneously prevent the hard frame from being fixed firmly in place on the extremity, cause undesired migration of the orthosis, reduce the necessary mechanical application of force or coupling of the hard frame and extremity and thus reduce the support effect of the orthosis or render it completely ineffective. Similar functional relationships and related problems exist in knee joint orthoses and also in wrist and ankle joint orthoses as well as in elbow joint orthoses.

There was therefore the technical problem of further developing a known hard frame as a component for such joint orthoses in such a way that they can be worn without any problem and the full functionality of the orthoses can be maintained without causing undesirable or harmful pressure or shear stress on the adjacent tissues of the extremity, and at the same time an undesirable migration of the orthosis is effectively suppressed.

The underlying technical problem is solved by a hard frame for an extremity joint orthosis according to claim 1. This has in particular two mutually opposed longitudinal joint splints, each of which, starting from its central, in particular multiaxial, joint, has two joint arms which extend in the proximal direction and distal direction when the orthosis is in the applied state. The joint arms of the joint splints are connected to one another by bridges to form the hard frame for the orthosis. The bridges are arched to tightly surround the respective proximal or distal section of the extremity. They form an essential part of the extremity holder. A tension belt is preferably provided to achieve complete frictional engagement on the holder with the respective extremity section; alternatively or additionally, the hard frame is preferably equipped with a tight-fitting elastic joint bandage in order to be fixed on the extremity. Indications for such hard frame orthoses are, in addition to joint arthrosis or joint misalignment, primarily also the functional support after surgery for the treatment of torn ligaments or cartilage defects.

According to the invention, it is now provided that at least one of the bridge arches connecting the joint splints is pivotably mounted on the arms of the joint splints which it connects in each case. It is provided according to the invention that this mounting allows the pivoting of this frame bridge at least about that pivot axis which is essentially parallel to the connecting line between the two joint arms connected via this bridge; that is to say, this pivot axis extends toward the connection of the two joint arms each connected via this bridge arch. The mounting according to the invention of at least one of the two bridges connecting the arms of the joint splints allows the arched bridge to be tilted favorably in the direction of pivoting of the joint splints, that is to say in the direction of the flexion or extension of the joint when the orthosis is in the applied state. In particular, the tilting of the bridge allows inevitable changes in the relative position of the holder with respect to the extremity that occur during flexion or extension to be compensated for and offset because of the elasticity of the tissue during flexion or extension, on the one hand, and because of the inelasticity of the supporting hard frame, on the other hand. A frictional movement of the hard frame bridge on the extremity holder due to shear forces and a pressure load occurring through the edges of the bridge arch because of unfavorable articulation angles of the bridge arch with respect to the surface of the extremity can be reduced or completely prevented. This is particularly relevant and efficient when using an overall rigid, i.e. inelastic and torsionally rigid, bridge arch.

Accordingly, the subject matter of the invention is a hard frame for a joint-bridging extremity joint orthosis, containing two mutually opposed longitudinal joint splints which are connected to one another via their proximal joint arms via a transverse proximal bridge arch and there form a proximal extremity holder there and furthermore are connected to one another via their distal joint arms via a transverse distal bridge arch and there form a distal extremity holder, characterized in that at least one of the bridge arches is in particular rigid and according to the invention is pivotably mounted on joint arm ends of the connected joint arms in joints about at least one pivot axis, this pivot axis extending toward the connection of the two joint arms that are connected to this bridge arch.

In particular, it is provided that the joint between the respective ends of the joint-mounted bridge arch and the ends of the steering arm connected thereto is realized in the simplest case by a joint pin, which thus forms a simple axial joint. In the simplest case, the flat material of the joint arm end is riveted or screwed or in a similar manner joined to the flat material of the end of the bridge arch at one point in order to form this axial joint. It is preferably provided that joint arm end and the end of the bridge arch connected thereto overlap flatly and slide against one another there when the bridge arch is pivoted against the joint arm end. In this way a determination is also made in particular of the direction of the pivot axis, and specifically perpendicular to the surface of the flat joint arm end on which the end of the bridge arch slides.

Accordingly, the subject matter of the invention is preferably also a hard frame according to the invention, the joints for pivoting in the at least one pivot axis each being formed between end sections of the rigid bridge arch and the joint arm ends overlapping therewith, the end sections being rotatably coupled to the joint arm ends in each case with a pivot pin.

In a first variant, the proximal bridge arch runs on the front (extended side) of the extremity when it is in the applied state; in the embodiment as or in a knee orthosis, thus, in the region of the shin. In an alternative variant, the proximal bridge arch runs on the back (flexion side) of the extremity in the applied state; in the embodiment as or in a knee joint orthosis, that is, in the region of the outer and inner calf muscles, and there lie firmly on the muscle bellies, which serve as soft tissue pads when the force is applied.

In one variant, the distal bridge arch runs on the front (extended side) of the extremity when it is in the applied state; in the embodiment as or in a knee joint orthosis, i.e. in the region of the rectus femoris as well as the vastus externus and vastus medialis and there lie firmly on the muscle bellies, which serve as soft tissue cushions when force is applied. In an alternative variant, the distal bridge arch runs on the back (flexion side) of the extremity when it is in the applied state; in the embodiment as or in a knee joint orthosis, i.e. in the region of the sinew muscle, the two-headed thigh muscle and the large puller muscle, and there they are particularly firmly attached to the muscle bellies, which serve as soft tissue pads when the force is applied. The distal bridge arch of the hard frame runs particularly preferably on the front, and the proximal bridge arch runs on the back of the extremity, in the embodiment as or in a knee joint orthosis, i.e. in the region of the calf muscles.

The pivoting preferably takes place in the rotational direction wherein the upper edge of the bridge arch can tip away from the bridged joint, in particular to compensate for a shortening of the effective length of the hard frame on the rear side (flexion side) of the extremity and/or an elongation of the effective length of the hard frame on the front side (extension side) that occur when the extremity is flexed. According to the invention, pressure loads otherwise occurring as a result through the edges of the, in particular, rigid bridge arch can be avoided. In the embodiment of the hard frame as or in a knee joint orthosis, the proximal bridge, which when it is in the applied state surrounds the lower leg, in particular in the region of the back side, i.e. on the calf, is in particular pivotable. The pivotability allows the bridge to move proximally out of a normal position toward the proximal in order to prevent or reduce shear and pressure loads on the calf when the knee is flexed.

Preferably, only the distal bridge is pivotable, and in this case the proximal bridge is preferably rigidly connected to the two proximal joint arms of the joint splints and, more preferably, is formed with them as a one-piece unit. Alternatively, only, or in one variant additionally, the proximal bridge is pivotable and the distal bridge can be rigidly connected to the two distal joint arms of the joint splints and, more preferably, can be formed as a one-piece unit with them. In a further embodiment, the proximal bridge and the distal bridge are pivotably mounted on the respective joint arms of the joint splints.

However, an embodiment is particularly preferred in which the distal bridge, which is in particular rigid and which is connected in particular with a knee orthosis in the applied state on the calf muscles, is at least always pivotable. In an alternative embodiment as or in a wrist orthosis, it is particularly provided that at least the proximal bridge, which in particular is rigid and rests against the forearm muscles in the applied state, is pivotable. In a further embodiment, as or in a wrist orthosis, it is alternatively particularly provided that at least the distal bridge, which is in particular rigid and in the applied state rests against the metacarpus, is pivotable.

In a particularly preferred embodiment, it is provided that the degree of pivoting of the bridge arch at the respectively connected joint arm ends is limited in the at least one pivot axis. The pivoting limitation allows only a certain movement of the bridge arch on the extremity holder, in particular to compensate for the aforementioned relative movements of the extremity at the holder relative to the orthosis during flexion or extension, but yet to ensure a sufficiently strong mechanical coupling between the extremity and the hard frame. In a first variant, the pivoting limitation is realized by a hard stop. An elongated hole is particularly preferably provided at the respective ends of the bridge arch, in which a sliding bolt, which is connected to the respective joint arm end in a stationary manner, can slide. Alternatively or additionally, the elongated hole is formed on the joint arm end, and the sliding bolt is formed on the end of the bridge arch. Alternatively or additionally, a mechanical stop is provided on the side arm end and/or on the bridge arch, an outer edge of the one joint element engaging with a projection of the other joint element in order to form the pivoting limitation.

The pivoting of the bridge out of the neutral position is preferably limited to approximately 20° or to approximately 15°. It is particularly preferred, however, to design the angle of the pivoting limitation differently depending on the use and application of the hard frame, that is to say particularly depending on the movement profile of the wearer and/or on the therapeutic objective. This means, in particular, the pivoting limitation can be less restrictive, especially limited to 12° to 20°, if great mobility is to be maintained when the orthosis is worn or the pursued therapeutic objective is not particularly strict. On the other hand, the pivoting limitation can be restrictive and limited to a few angular degrees, especially 5° to 12°, if an increased support effect by the orthosis is desired or the mobility of the wearer is already restricted. A variable pivoting limitation, which can extend to the optional total blocking of the joint, can be achieved in a manner known per se. In the case of an embodiment having a bolt sliding in an elongated hole, wherein the elongated arch length is constant, different insertion points of one or more sliding bolts or, alternatively or additionally, the formation of elongated holes of different lengths which can optionally be selected by inserting the sliding bolt are preferable.

In a preferred embodiment it is alternatively or additionally provided that the joint movement on the joint formed between the joint arm end and the bridge arch is mechanically inhibited in order to counteract the pivoting of the bridge arch with a mechanical resistance. This preferably means that on the one hand the pressure load on the tissue on the extremity holder is sufficiently reduced, but on the other hand the bridge on the socket still ensures sufficient mechanical resistance for a functional mechanical coupling of the hard frame to the extremity. This pivoting restraint is preferably achieved by mechanical friction between the end sections of the bridge arch and the joint arm ends connected to it in each case via the joint. It is preferably provided that at least one of the two joint elements has a friction lining, whereby the mechanical friction on the joint is modified, preferably increased. Alternatively or additionally, it is provided that the joint splint and the overlapping end section of the bridge are knurled around the pivot pin or are provided with teeth in order to increase the friction by this surface texturing. It is particularly provided that the teeth form a detent so that the bridge only further pivots a catch starting at a certain force input and, thus, the usual rigid guiding function of the bridge remains constant in the context of only light force inputs which do not yet overcome the detent resistance.

In an alternative or additional preferred embodiment, it is provided that the joint between the joint arm end and the bridge arch is formed exclusively or additionally by an elastomer block formed between these two elements. This advantageously serves on the one hand to mechanically restrain the pivoting movement, but on the other hand also to use a pivoting limitation which depends on the pivoting angle and which starts gently. The elastomer block is a torsion joint with spring and damping effects. Preferred elastomer materials are silicone elastomers and polyurethane elastomers. In a special variant, thermosensitive polymers are provided which become more flexible with increasing mechanical stress. This enables automatic adjustment of the degree of pivoting and the pivoting restraint to the respective state of motion. In analogous alternative configurations thereof, simple axial joints with a connected coil spring can be provided.

In a preferred embodiment, it is provided that at least one joint arm end, in particular where the joint arm end is connected to the pivotable bridge arch according to the invention, is formed as a leaf spring, that is, an elastic spring leaf, on the hard frame. This advantageously allows the joint arm end to be elastically tilted out of the plane of the longitudinal extension of the joint splint, that is to say particularly out of the primary pivoting plane of the joint splint. In particular in connection with a further fixable tilting joint in the joint splint with which at least one of the joint arms of the joint splint can be tilted out of the primary pivoting plane of the joint of the joint splint, this allows compensating for misalignments at the extremity joint transverse to the primary flexion and extension direction of the joint or actively guiding the extremity joint in this tilt. Such a fixable tilt joint can be formed as an additional axial joint in one or more of the joint arms, the axis of this tilt joint being oriented in the plane of the joint splint and transversely to the longitudinal extension of the joint splint. Alternatively or additionally, the fixable tilt joint can be formed next to, in or as part of the primary pivot joint of the joint splint.

It is provided in particular that the fixable tilt joint forces the permanently adjustable tilting of the joint arm out of the pivoting plane of the joint splint, and the spring leaf which is preferably additionally provided on the joint arm end of the respectively tilted joint arm compensates for this forced tilting in order to align the bridge arch strictly transverse to the longitudinal extension of the extremity, despite this lateral tilting. This makes it possible for the extremity holder formed by this bridge arch to always run transversely to the longitudinal extension of the extremity and thus with the smallest possible extent at this point. An undesirable migration of the hard frame, and thus the joint orthosis, by slippage of the holder is thus counteracted.

The hard frame construction described here with a tiltable bridge between the joint splints can be used particularly well in connection with knee joint orthoses, preferably at least the bridge arch for the distal extremity holder, that is to say for the socket of the lower leg, being rigidly formed and this bridge arch according to the invention being pivotably articulated on the distal joint arm ends of the two joint splints in the manner according to the invention. The pressure loads and shear forces that occur in particular on the lower leg when the knee during flexion or extension are largely or completely compensated for by the pivotable bridge arch, so that a secure lower leg holder is achieved which at the same time is not mechanically stressful for the wearer. A special subject matter of the present invention is therefore a knee joint orthosis which contains the hard frame according to the invention.

In an alternative embodiment, the joint orthosis which contains the hard frame according to the invention is a wrist orthosis. In a further alternative embodiment, the joint orthosis which contains the hard frame according to the invention is an elbow joint orthosis. In a further alternative embodiment, the joint orthosis which contains the hard frame according to the invention is an ankle orthosis or a foot lifting orthosis.

The invention is explained in more detail by the following exemplary embodiments, which are illustrated in the figures. The figures show preferred configurations which, in addition to the features according to the invention, showed further optional features. The latter are not to be understood as limiting the present invention, but rather show only practical and preferred embodiment variants.

FIG. 1 shows a perspective view of an embodiment of the hard frame 100 according to the invention as or for a knee joint orthosis. The hard frame 100 is essentially composed of two mutually opposed joint splints 110, 120 that overlap the joint. The outer joint splint 120 has essentially the same basic structure as the inner joint splint 110. The joint splints 110, 120 each have central joints 111, 121, which are formed in particular as a multiaxial joint in order to anatomically simulate the joint movement of the knee joint to be supported. In the joint splint 110, the proximal joint arm 113 and the distal joint arm 112 start from the central joint 111. These are coupled via the joint 111 and are pivotable relative to one another in a primary pivoting plane of the joint splint 110 in order to follow the joint movement. Analogously, in the case of the joint splint 120, the proximal joint arm 123 and the distal joint arm 122 start from the central joint 121, which are coupled via the joint 121 and are pivotable relative to one another in a primary pivoting plane of the joint splint 120 in order to follow the joint movement. The joint splints 110, 120 are connected to one another at the ends of the proximal joint arms 113, 123 via a proximal bridge 310 and at the ends of the distal joint arms 112, 122 via a distal bridge 210, in order to finally form the hard frame 100.

In the illustrated embodiment, a fixable tilt joint 115 is additionally provided on each of the distal joint arms 112 and 122. This fixable tilt joint 115 enables the respective joint arm 112, 122 to be tilted out of the primary pivoting plane of its joint splint 110, 120.

According to the invention, the distal bridge 210 is pivotably mounted on the joint arm ends 114 and 124 of the distal joint arms 112 in the embodiment shown. According to the invention, the joint arm end 114 is connected to an overlapping end section 212 of the bridge 210 via a fixed rivet, which serves as a pivot pin 224, and is rotatably supported there in a bearing bush formed in the end section 212, thereby forming an axial joint 220 on which the bridge 210 is pivotally mounted on the joint arm end 114. Likewise, the joint arm end 124 is connected to an overlapping end section 212 of the bridge 210 via a fixed rivet, which serves as an pivot pin 224, and thereby also an axial joint 220 is formed, via which the bridge 210 is also pivotably mounted on the joint arm end 124.

In order to achieve a preferred limitation of the pivoting limitation 223, a further rivet 226 is fixedly connected to the respective joint arm end 114, 124 and slides as a sliding pin 226 in an elongated hole 216, which is formed in the respective overlapping end section 212 of the mounted bridge 210. The elongated hole 216 serves as a stop for the sliding pin 226 and thus limits the degree of pivoting of the bridge 210.

Furthermore, in the embodiment shown, the respective joint arm end 114 and 124 is formed as a spring leaf, which is mechanically fixedly coupled to the joint arm 112 and 122 in each case via rivets 116. The pivot pin 224 and the sliding pin 226 are also correspondingly formed in the spring leaf.

Figure 2:
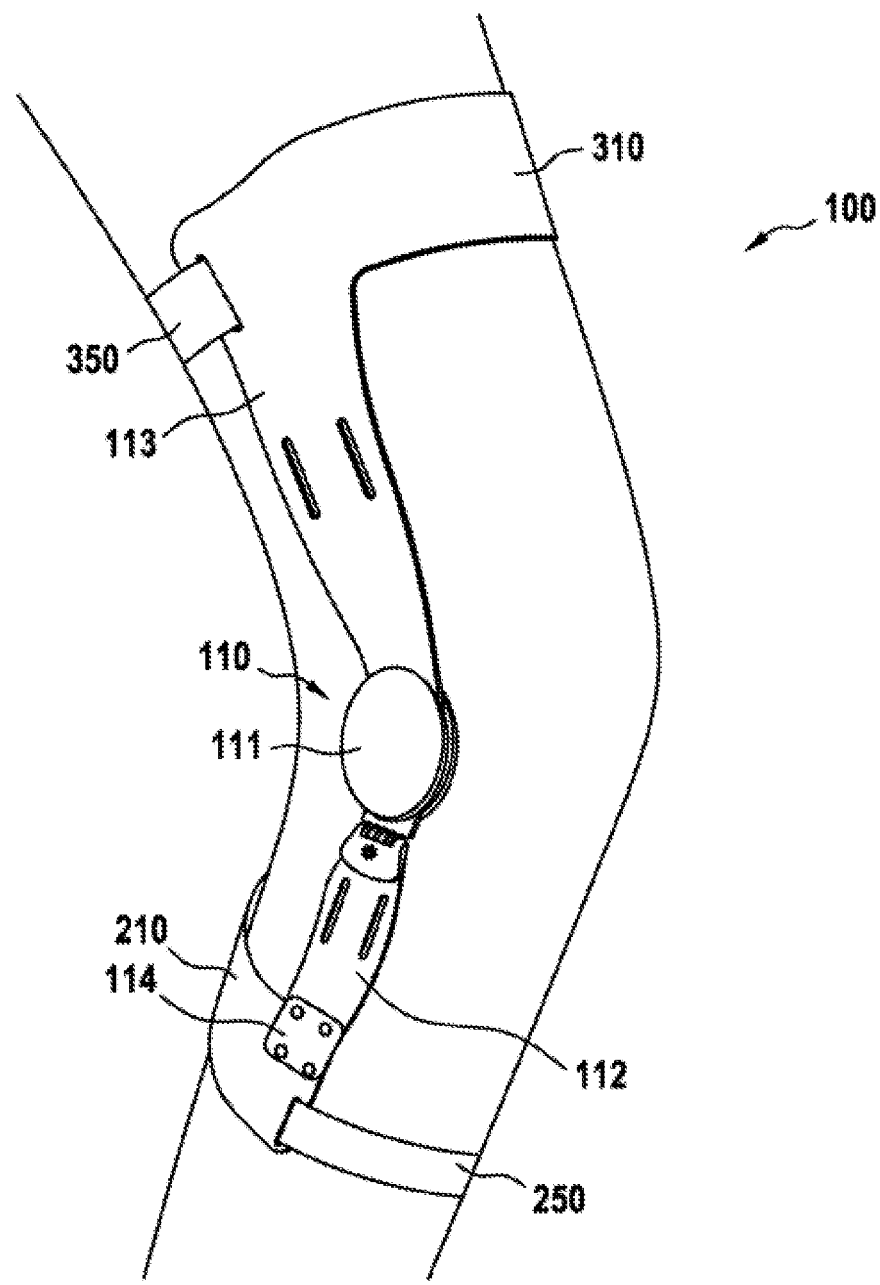

FIG. 2 shows a perspective view of an embodiment as a knee joint orthosis according to FIG. 1, applied over the schematically indicated knee. The reference numbers apply accordingly. The proximal bridge 310, together with the tension belt 350, forms a proximal extremity holder 300 that engages around the thigh in the applied state. The distal bridge 210 together with the tension belt 250 forms a distal extremity holder 200 which engages around the lower leg in the applied state. In the embodiment shown, the hard frame 100 is mechanically firmly connected to the extremity via the straps 250, 350 and the bridges 210, 310 in order to achieve sufficient force introduction for the support function of the orthosis.

Figure 3:
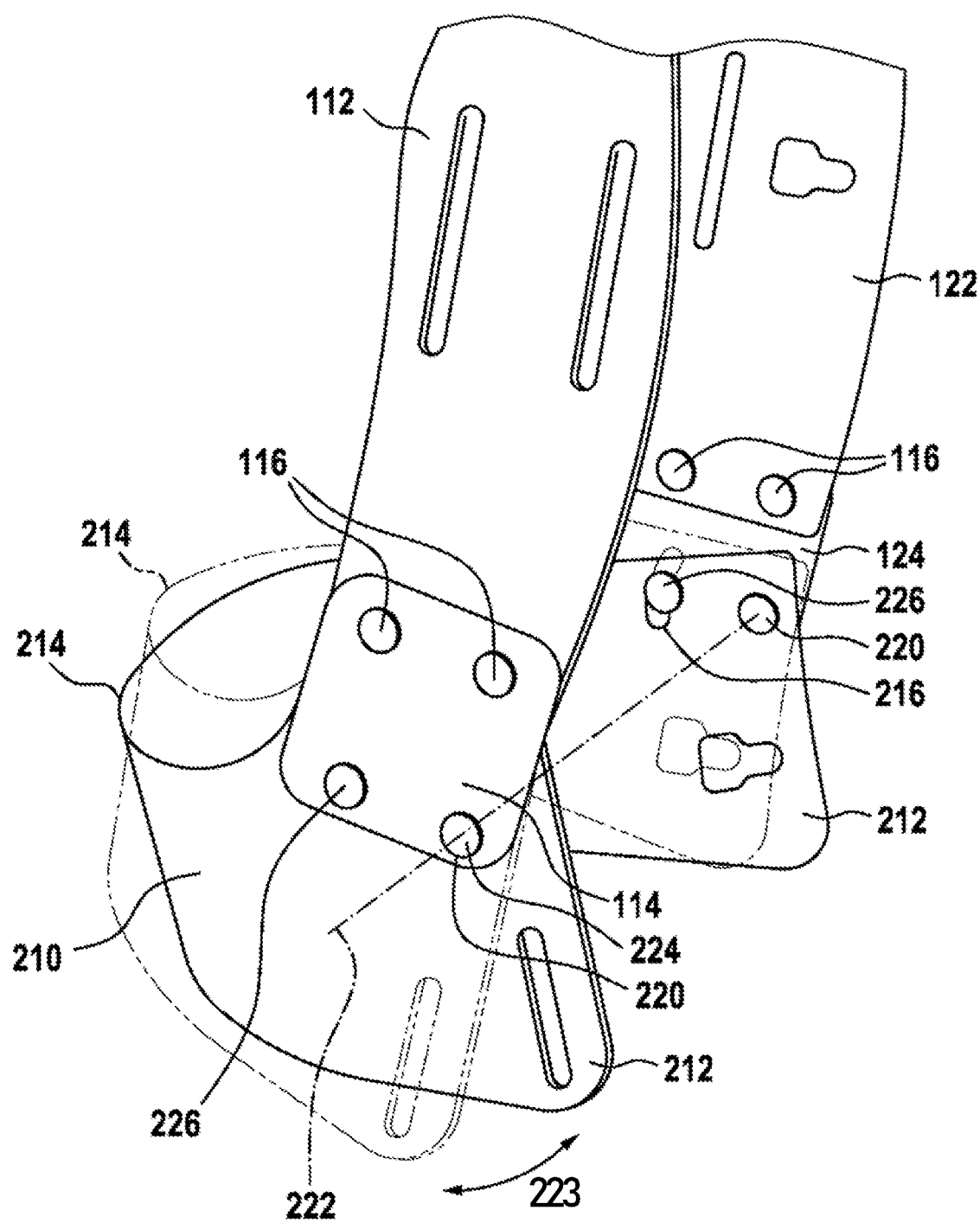

FIG. 3 shows a detailed view of the embodiment according to FIGS. 1 and 2. The distal bridge arch 210 can rotate according to the invention in the joints 220 in each case about the pivot axis 222. The respective pivot axes 222 of the joints 220 are shown schematically. The pivot axes 222 each run essentially perpendicular to the plane of the flat joint arm ends 114, 124. In particular, the upper edge 214 of the rigid bridge arch 210 can temporarily tip distally when used (dashed shape) in order to specifically compensate for a shear and pressure load on the lower leg of an applied knee orthosis, which occurs during movement, primarily when the knee is flexed.

Figure 4:
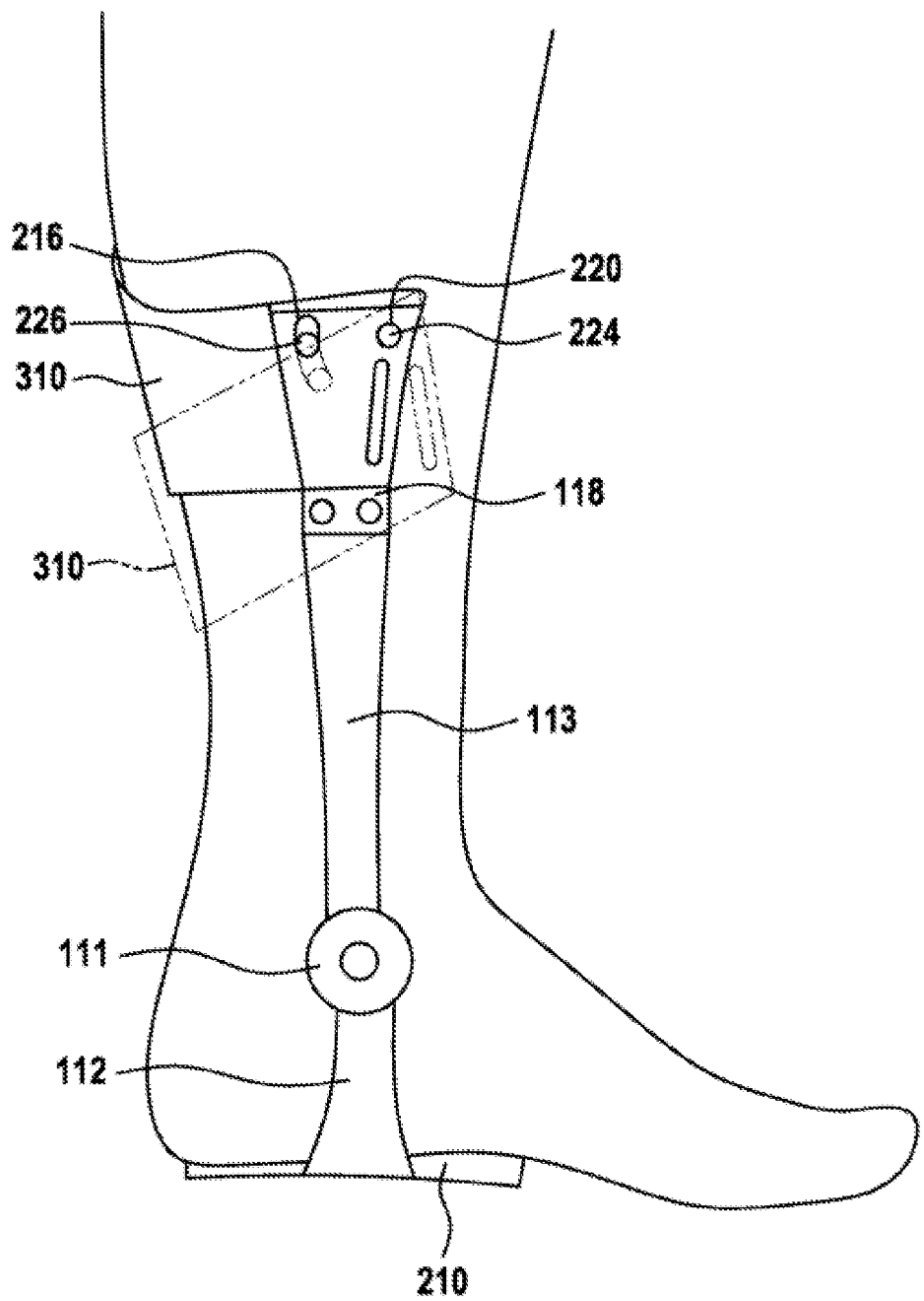

FIG. 4 shows an embodiment as an ankle orthosis. The reference numerals from FIGS. 1 to 3 apply to corresponding structures. In the hard frame according to FIG. 4, the proximal bridge arch 310 is pivotably mounted on the joint 220, which is formed by the rivet 224 on the proximal joint arm end 118.

Figure 5:
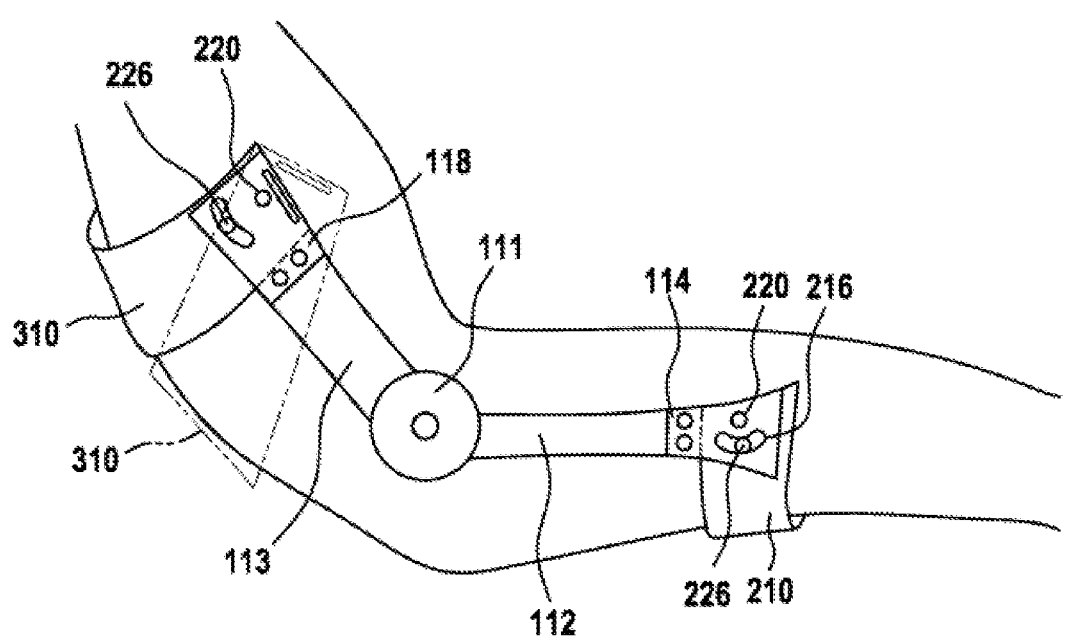

FIG. 5 shows an embodiment as a wrist orthosis. The reference symbols from FIGS. 1 to 4 apply to corresponding structures. In the hard frame according to FIG. 5, the proximal bridge arch 310 is pivotably mounted on the proximal joint arm end 118 via the joint 220, and the distal bridge arch 210 is pivotably supported on the distal joint arm end 114 via the joint 220.

The invention claimed is:

1. A hard frame (100) for a joint-bridging extremity joint orthosis, comprising: two mutually opposed longitudinally extending joint splints (110, 120), which are connected to one another via their proximal joint arms (113, 123) via a transverse proximal bridge arch (310) and there form a proximal extremity holder (300) and further are connected to one another via their distal joint arms (112, 122) via a transverse distal bridge arch (210) and there form a distal extremity holder (200), wherein the joint splits (110, 120) each has a central joint (111, 121), and belt straps (350, 250) configured for fixing an extremity to be supported on the respective proximal and distal holders (300, 200) of the hard frame (100), wherein at least one of the proximal and distal bridge arches (210, 310) is rigid and is pivotably mounted on each joint arm ends (114, 124) of the connected distal and/or proximal joint arms (112, 122) in joints (220) about at least one pivot axis (222), and this pivot axis (222) extends toward the connection of the two joint arms (112, 122) connected via the respective rigid proximal and/or distal bridge arch (210), wherein each of the joints (220) for pivoting the at least one of the proximal and distal bridge arches about the at least one pivot axis (222) is limited by an elongated hole (216) in end sections (212) of the rigid proximal and/or distal bridge arch (210) and a sliding pin (226), the sliding pin (226) is fixed to the respective joint arm end (114, 124) and slides in the elongated hole (216), and the elongated hole (216) is oriented in a vertical direction and limits a pivoting range of the at least one of the proximal and distal bridge arches to 5 degrees to 20 degrees, wherein at least one joint arm end (114, 124) is formed as a spring leaf, which allows a resilient tilting of this joint arm end (114, 124) from a primary pivoting plane of the joint splint (110, 120), the at least one joint arm end (114, 124) is mechanically fixedly coupled to the corresponding joint arm (112, 122) using a pair of rivets (116), and the sliding pin (226) and a pivot pin (224) are also correspondingly formed at a posterior and anterior position, respectively, in the at least one joint arm end (114, 124), and wherein at least one fixable tilting joint (115) is additionally formed in at least one of the joint splints (110, 120) for tilting at least one of the joint arms (112, 113, 122, 123) from the primary pivoting plane of the at least one of the respective joint splints (110, 120).

2. The hard frame (100) according to claim 1, wherein the joint (220) has a mechanical restraint which resists the pivoting.

3. The hard frame (100) according to claim 2, wherein the mechanical restraint is effected by engaging end sections (212) of the rigid bridge arch (210) and the joint arm ends (114, 124) respectively connected to one another so as to overlap.

4. The hard frame (100) according to claim 3, wherein the restraint is brought about by mechanical friction between end sections (212) of the rigid bridge arch (210) and the joint arm ends (114, 124) connected to one another so as to overlap.

5. The hard frame (100) according to claim 1, wherein the joints (220) for pivoting about the at least one pivot axis (222) are each formed between end sections (212) of the rigid bridge arch (210) and the joint arm ends (114, 124) overlapping therewith, wherein the end sections (212) having the joint arm ends (114, 124) are each rotatably coupled to one another via the pivot pin (224), wherein the end sections (212) of the distal rigid bridge arch (210) and the respective joint arm ends (114, 124) are elastically coupled to one another.

6. The hard frame (100) according to claim 1, wherein the joint orthosis is a knee joint orthosis.

7. A hard frame (100) for a joint-bridging extremity joint orthosis, comprising: two mutually opposed longitudinally extending joint splints (110, 120), which are connected to one another via their proximal joint arms (113, 123) via a transverse proximal bridge arch (310) and there form a proximal extremity holder (300) and further are connected to one another via their distal joint arms (112, 122) via a transverse distal bridge arch (210) and there form a distal extremity holder (200), wherein the joint splints (110, 120) each has a central joint (111, 121), and belt straps (350, 250) configured for fixing an extremity to be supported on the respective proximal and distal holders (300, 200) of the hard frame (100), wherein at least one of the proximal and distal bridge arches (210, 310) is rigid and is pivotably mounted on each joint arm end (114, 124) of the connected distal and/or proximal joint arms (112, 122) in joints (220) about at least one pivot axis (222), and this pivot axis (222) extends toward the connection of the two joint arms (112, 122) connected via the respective rigid proximal and/or distal bridge arch (210), wherein a limit of each of the joints (220) for pivoting the at least one of the proximal and distal bridge arches about the at least one pivot axis (222) consists of an elongated hole (216) in end sections (212) of the rigid proximal and/or distal bridge arch (210) and a sliding pin (226), the sliding pin (226) is fixed to the respective joint arm end (114, 124) and slides in the elongated hole (216), and the elongated hole (216) is oriented in a vertical direction and limits a pivoting range of the at least one of the proximal and distal bridge arches to 5 degrees to 20 degrees, wherein at least one joint arm end (114, 124) is formed as a spring leaf, which allows a resilient tilting of this joint arm end (114, 124) from a primary pivoting plane of the joint splint (110, 120), the at least one joint arm end (114, 124) is mechanically fixedly coupled to the corresponding joint arm (112, 122) using a pair of rivets (116), and the sliding pin (226) and a pivot pin (224) are also correspondingly formed in the at least one joint arm end (114, 124), and wherein at least one fixable tilting joint (115) is additionally formed in at least one of the joint splints (110, 120) for tilting at least one of the joint arms (112, 113, 122, 123) from the primary pivoting plane of the at least one of the respective joint splints (110, 120).

\* \* \* \* \*